(12) United States Patent
Voudouris

(10) Patent No.: US 10,603,138 B2
(45) Date of Patent: Mar. 31, 2020

(54) SELF-LIGATING ORTHODONTIC BRACKET

(71) Applicant: John C. Voudouris, Toronto (CA)

(72) Inventor: John C. Voudouris, Toronto (CA)

(73) Assignee: ORTHOARM INCORPORATED, Toronto, Ontario (CA)

( * ) Notice: Subject to any disclaimer, the term of this patent is extended or adjusted under 35 U.S.C. 154(b) by 0 days.

(21) Appl. No.: 14/149,585

(22) Filed: Jan. 7, 2014

(65) Prior Publication Data

US 2014/0308622 A1    Oct. 16, 2014

Related U.S. Application Data

(63) Continuation of application No. 12/477,824, filed on Jun. 3, 2009, now Pat. No. 8,636,507.

(51) Int. Cl.
*A61C 7/28* (2006.01)
*A61C 7/14* (2006.01)

(52) U.S. Cl.
CPC ............... *A61C 7/287* (2013.01); *A61C 7/14* (2013.01)

(58) Field of Classification Search
CPC .... A61C 7/12; A61C 7/14; A61C 7/28; A61C 7/141; A61C 7/143; A61C 7/146; A61C 7/148; A61C 7/00–36
USPC ...................................... 433/8–24
See application file for complete search history.

(56) References Cited

U.S. PATENT DOCUMENTS

| 5,562,444 | A | 10/1996 | Heiser et al. |
| 6,368,105 | B1 | 4/2002 | Voudouris et al. |
| 6,776,613 | B2 * | 8/2004 | Orikasa ............. A61C 7/287 433/11 |
| 6,939,133 | B2 * | 9/2005 | Voudouris ........... A61C 7/02 433/11 |

(Continued)

FOREIGN PATENT DOCUMENTS

DE    20 2004 017 952 U1    5/2005

OTHER PUBLICATIONS

Orthoarm Incorporated against Dentsply GAC International and Dentsply Sirona Inc. Defendants' Invalidty Contentions dated Mar. 27, 2017; 3 pp.

(Continued)

*Primary Examiner* — Yogesh P Patel
(74) *Attorney, Agent, or Firm* — Fox Rothschild LLP

(57) ABSTRACT

A self-ligating orthodontic bracket comprising a body and a locking shutter. A mesio-gingival reference plane is defined tangent to a lingual-most point of the archwire slot. The body further includes an occlusal-gingival opening that intersects the reference plane. The locking shutter includes a lingual end located in the opening at a closed lingual location when the locking shutter is in a closed position, and at an open lingual location when the locking shutter is in an open position. The locking shutter further includes a labial end located at a closed labial location when the locking shutter is in the closed position and at an open labial location when the locking shutter is in the open position. A first occlusal-gingival distance from the closed lingual location to the open lingual location is at least about 70% of a second occlusal-gingival distance from the closed labial location to the side surface. In addition, the first occlusal-gingival distance is at least about 60% of a third occlusal-gingival (Continued)

distance from the closed lingual location to an end of a tie wing.

17 Claims, 5 Drawing Sheets

(56) References Cited

U.S. PATENT DOCUMENTS 7,442,039 B2   10/2008   Opin et al.
7,993,132 B2    8/2011   Opin et al.

OTHER PUBLICATIONS

Self-Ligating Brackets in Lingual Orthodontics by Silvia Geron Seminars in Orthodontics, vol. 14, No. 1 (Mar. 2008); pp. 64-72.
Joint Status letter to the Court for the Eastern District of New York dated Nov. 8, 2016; 5 pp.

* cited by examiner

SELF-LIGATING ORTHODONTIC BRACKET

BACKGROUND

The present invention relates generally to the field of orthodontics and, more specifically, to the field of orthodontic bracket assemblies.

According to established orthodontic techniques, it is well known to attach an orthodontic bracket assembly to a patient's tooth. The bracket assembly provides a location for attaching an archwire and other orthodontic devices to facilitate movement of the tooth. According to established orthodontic techniques, it is well known to ligate an archwire to the orthodontic bracket assembly utilizing an elastic or metal ligature. In conventional orthodontic bracket assemblies, the ligature is wrapped around respective gingival and occlusal tie wings so as to overlay the archwire at mesial and distal ends of the orthodontic bracket assembly.

Recently, designers have created self-ligating bracket assemblies that do not require a separate ligature for attachment of the archwire to the bracket assembly. One type of self-ligating bracket assembly is supplied with a locking shutter that is movable between an open position, permitting access to the archwire slot, and a closed position, inhibiting access to the archwire slot. Self-ligating bracket assemblies substantially decrease the time involved in performing ligation procedures.

SUMMARY

The present invention provides a self-ligating orthodontic bracket comprising a body and a locking shutter. The body has an archwire slot defined at least partially by a side surface (e.g., a gingival side surface) and a lingual surface, and a mesio-gingival reference plane is defined tangent to a lingual-most point of the lingual surface. The body further includes an occlusal-gingival opening that intersects the reference plane. The locking shutter is coupled to the body and movable between a closed position where access to the archwire slot is inhibited and an open position where access to the archwire slot is permitted. The locking shutter includes a lingual end located in the opening at a closed lingual location when the locking shutter is in the closed position, and wherein the lingual end is located at an open lingual location when the locking shutter is in the open position. The locking shutter further includes a labial end located at a closed labial location when the locking shutter is in the closed position and at an open labial location when the locking shutter is in the open position, wherein the side surface is closer to the open labial location than to the closed labial location. A first occlusal-gingival distance from the closed lingual location to the open lingual location is at least about 70% of a second occlusal-gingival distance from the closed labial location to the side surface. Preferably, the first occlusal-gingival distance is at least about 80%, and more preferably at least about 90%, of the second occlusal-gingival distance.

In one embodiment, the body further includes a lingual resting groove in which the lingual end of the locking shutter is positioned when the locking shutter is in the open position. In this embodiment, the resting groove is positioned outside of the occlusal-gingival opening.

In another embodiment, the opening is in a first side of the body, and the body further includes at least one tie wing on the first side of the body. In this embodiment, the locking shutter is substantially free of contact with the tie wing when the locking shutter is in the open position.

In another aspect, the present invention provides a self-ligating orthodontic bracket comprising a body and a locking shutter, as generally described above. The body has an archwire slot defined at least partially by a lingual surface, and a mesio-gingival reference plane defined tangent to a lingual-most point of the lingual surface. The body further includes an occlusal-gingival opening in a first side of the body and intersecting the reference plane. The body further includes at least one tie wing on the first side of the body. The locking shutter is coupled to the body and movable between a closed position where access to the archwire slot is inhibited and an open position where access to the archwire slot is permitted. The locking shutter includes a lingual end located in the opening at a closed labial location when the locking shutter is in the closed position, and wherein the lingual end is located at an open lingual location when the locking shutter is in the open position. A first occlusal-gingival distance from the closed lingual location to the open lingual location is at least about 60% of a second occlusal-gingival distance from the closed lingual location to an end of the tie wing. Preferably, the first occlusal-gingival distance is at least about 65%, and more preferably at least about 70%, of the second occlusal-gingival distance.

Other aspects of the invention will become apparent by consideration of the detailed description and accompanying drawings.

DETAILED DESCRIPTION

Figure 1:
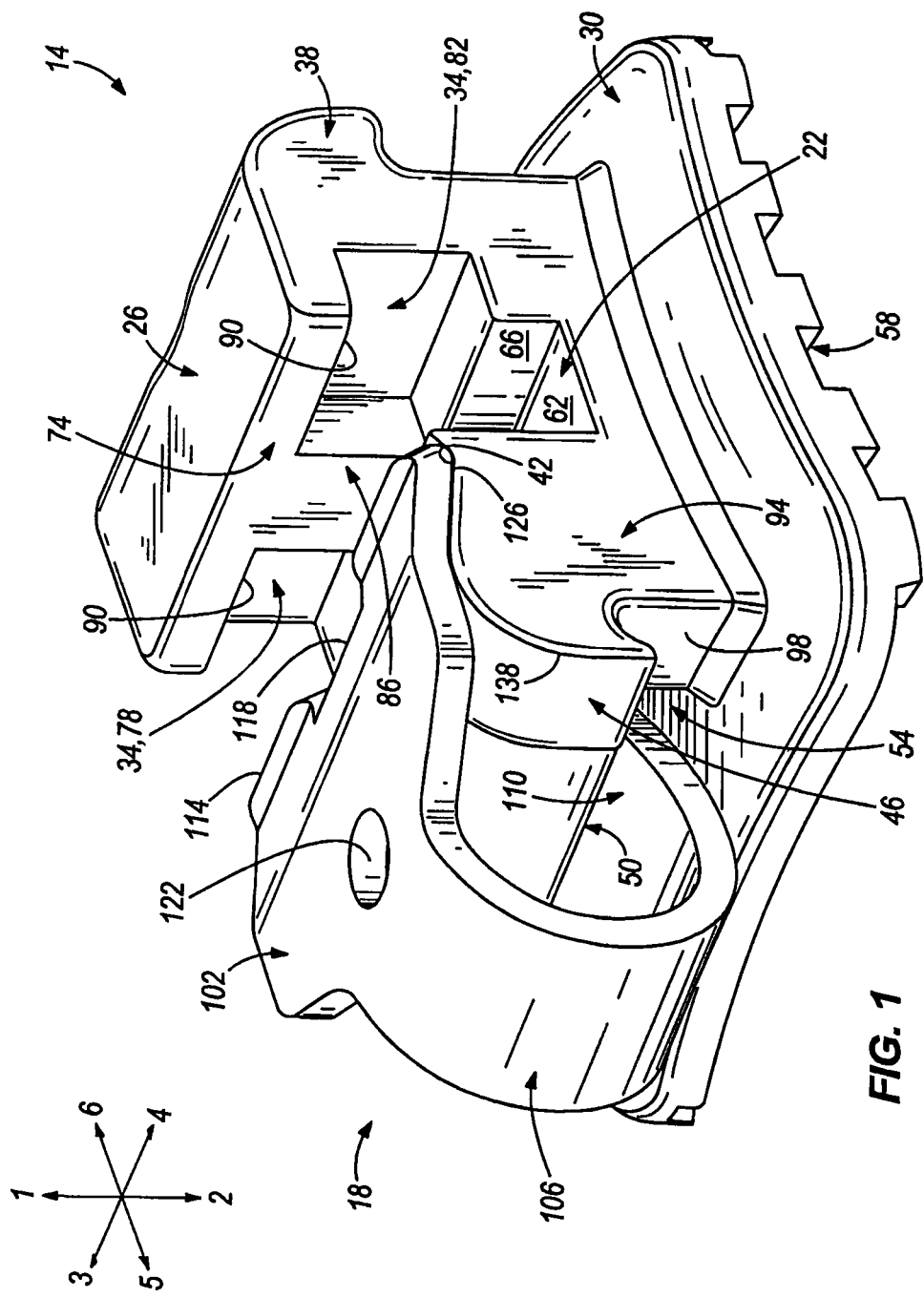
FIG. 1 is a perspective view of a self-ligating orthodontic bracket.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following description will refer to FIGS. 1-7, each including a reference axis with four or more reference directions. The reference directions are labeled 1-6 as follows: a labial direction 1, a lingual direction 2, a distal direction 3, a mesial direction 4, an occlusal direction 5, and a gingival direction 6. The illustrated reference directions are intended to clarify the description and do not in any way limit the scope of the invention. In other embodiments, the reference directions may be other than are shown or arranged differently.

FIG. 1 illustrates a self-ligating orthodontic bracket assembly that includes a bracket 14 and a locking shutter 18. The bracket 14 has a closed position (broken lines in FIGS. 5 and 6) in which the shutter 18 inhibits access to an archwire slot 22 and an open position (FIGS. 1, 2, 4, and solid lines in FIGS. 5 and 6) in which the shutter 18 allows access to the archwire slot 22.

The illustrated bracket 14 includes a body 26 and a base 30. The illustrated body 26 includes the archwire slot 22, two receiving areas 34, a first tie wing 38, a labial resting groove 42, a second tie wing 46, a lingual resting groove 50, and an occlusal-gingival opening 54. The illustrated base 30 connects the bracket 14 to a tooth (not shown) and includes an attachment portion 58 that defines a pattern (see FIG. 3) which receives an adhesive and is shaped to affix to the tooth. In the illustrated embodiment, the lingual side of the attachment portion 58 affixes to the labial side of the tooth. In the illustrated construction, the base 30 is attached to the body 26 with welds. In other constructions, the base 30 may be attached in other ways or formed as a single piece with the body 26.

Figure 2:
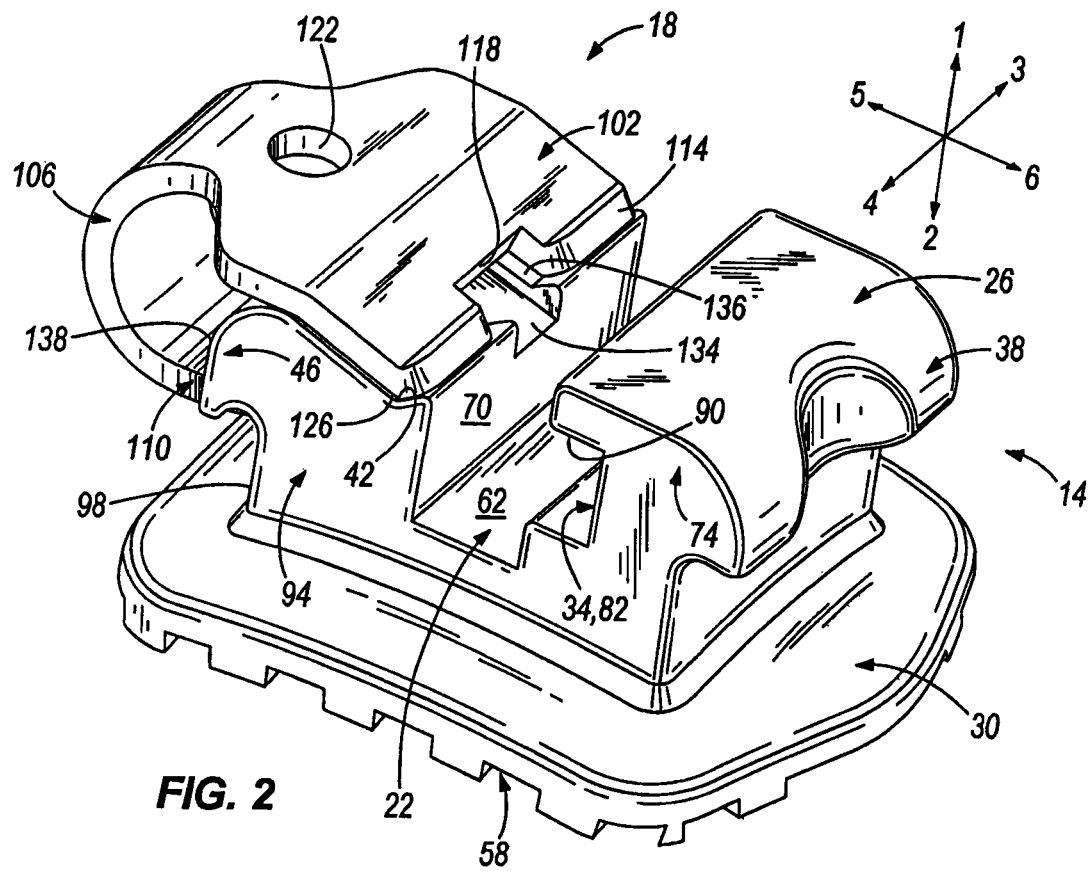
FIG. 2 is another perspective view of the self-ligating orthodontic bracket of FIG. 1.
Figure 3:
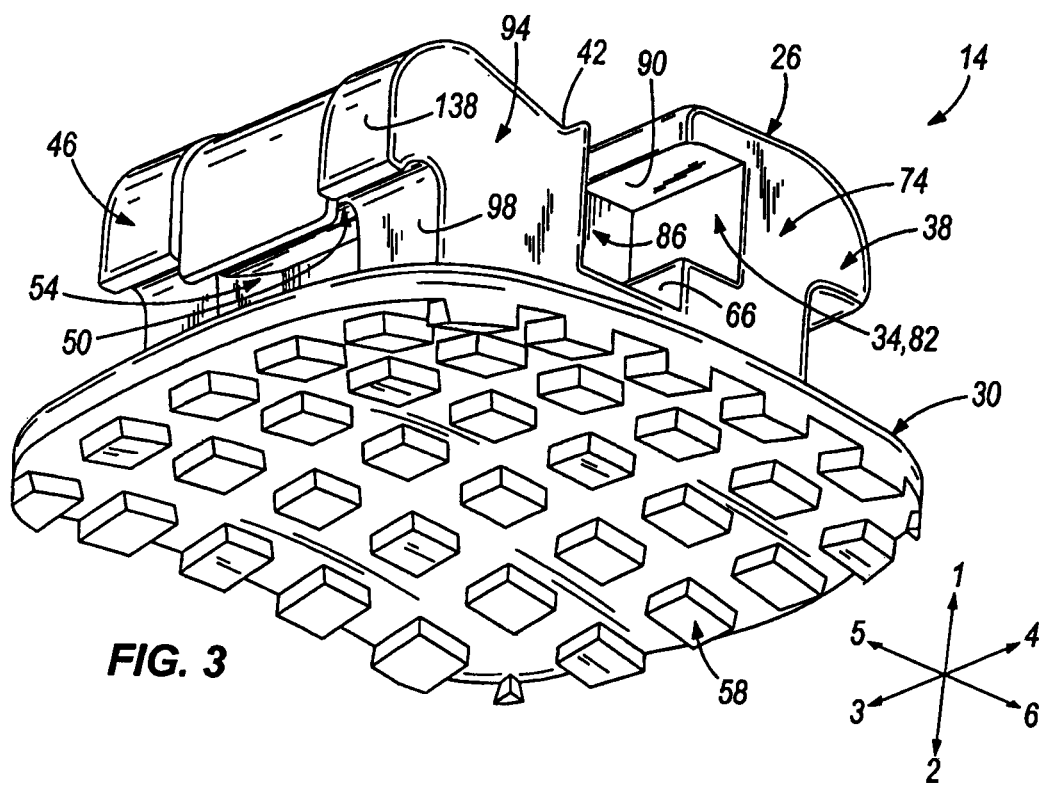
FIG. 3 is a perspective view of the self-ligating orthodontic bracket of FIG. 1 with a locking shutter removed.
Figure 4:
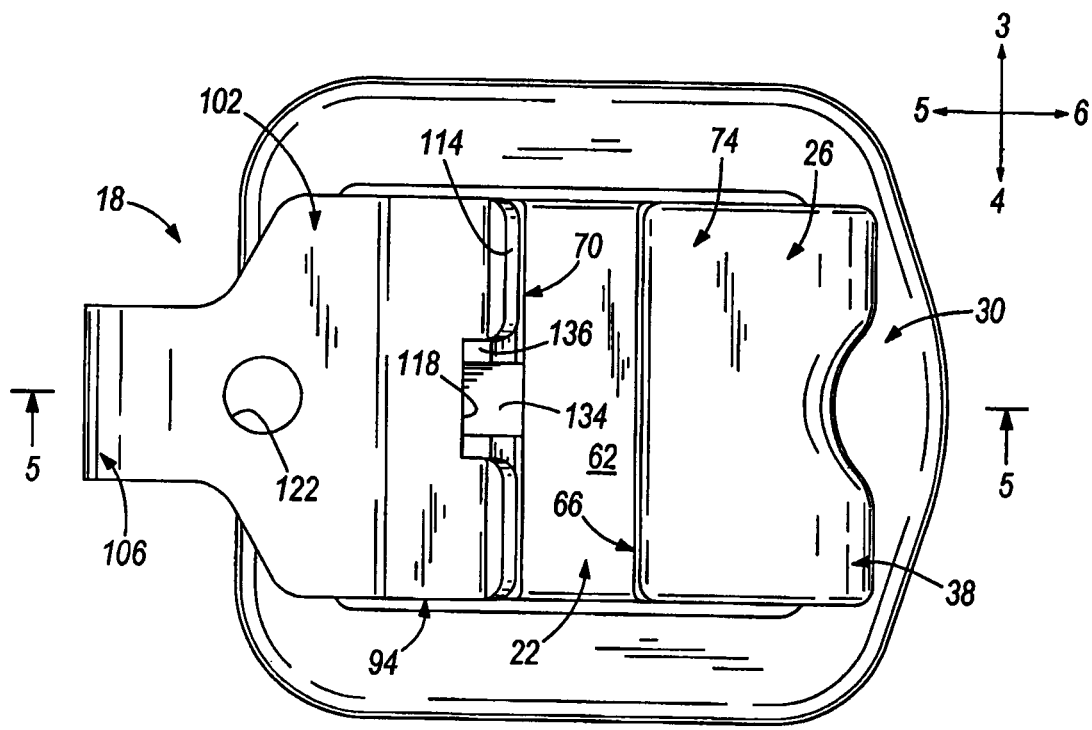
FIG. 4 is a top view of the self-ligating orthodontic bracket of FIG. 1.

The illustrated archwire slot 22 is defined by a lingual surface 62, a gingival side surface 66, and a occlusal side surface 70 (see FIG. 2). In the illustrated embodiment, a mesio-gingival reference plane 72 (see FIG. 5) is tangent to a lingual-most point of the lingual surface. The archwire slot 22 receives an archwire (not shown) and inhibits movement of the archwire in the lingual, gingival, or occlusal directions.

The illustrated receiving areas 34 are defined in a gingival portion 74 of the body 26 and include a first receiving area 78 separated from a second receiving area 82 by a protrusion 86. The first receiving area 78 extends labially and gingivally from the gingival side surface 66 to a retention lip 90 on one of the mesial or distal sides of the body 26. The second receiving area 82 extends labially and gingivally from the gingival side surface 66 to the retention lip 90 on the other of the mesial or distal sides of the body 26. The protrusion 86 separates the first receiving area 78 and the second receiving area 82 mesio-distally and is gingivally even with the gingival side surface 66.

The illustrated first tie wing 38 is formed on the gingival portion 74 of the body 26 and provides a place for ligation bands or wire to be wrapped for functional or aesthetic purposes. The first tie wing 38 includes two wings although less that two wings or more than two wings are possible.

The illustrated second tie wing 46 is formed on an occlusal portion 94 of the body 26 and provides a place for ligation bands or wire to be wrapped for functional or aesthetic purposes. The second tie wing 46 includes one wing although more than one wing and less than one wing have been considered.

The illustrated labial resting groove 42 is defined as a lingually-depressed area in the occlusal portion 94 of the body 26. The labial resting groove 42 is engaged by the shutter 18 while in the open position. In other constructions, the labial resting groove 42 may be other shapes or may be removed.

The illustrated lingual resting groove 50 is defined as a labially-depressed area in the occlusal portion 94 of the body 26. The lingual resting groove 50 is engaged by the shutter 18 while in the open position. In other constructions, the lingual resting groove 50 may be other shapes or may be removed.

The illustrated occlusal-gingival opening 54 is defined in the occlusal portion 94 of the body 26, extends gingivally into the occlusal portion 94 of the body 26 from an occlusal side 98, and is positioned such that the mesio-gingival reference plane 72 intersects the occlusal-gingival opening 54. The occlusal-gingival opening 54 is sized to receive the shutter 18 when in the closed position.

With continued reference to FIG. 1, the illustrated shutter 18 includes a labial portion 102, an intermediate portion 106, and a lingual portion 110. The labial portion 102 is substantially the same mesio-distal width as the body 26 and includes a labial end 114, a notch 118, and a cut-out 122.

The illustrated labial end 114 of the shutter 18 is curved labially to form a convex surface 126 that fits in the labial resting groove 42 when the shutter 18 is in the open position. The notch 118 is defined in the labial end 114 and receives the protrusion 86 when the shutter 18 is in the closed position such that the shutter 18 is stabilized in the mesio-distal direction. In other constructions, the labial portion 102 may be different shapes or mesio-distal widths. In addition, the convex surface 126 and the labial end 114 may be different shapes or may be straight sections. Furthermore, the labial end 114 may define more than one notch 118 or less than one notch 118 and the body 26 may include more than one protrusion 86 or less than one protrusion 86 to be received in the notches 118 in the labial end 114.

The illustrated cut-out 122 is a circle that extends through the shutter 18 and receives a tool (i.e. an opening tool, not shown) that may be used to move the shutter 18 between the open position and the closed position. In other constructions, the cut-out 122 may be different shapes, may not extend through the shutter 18, or may be removed.

The illustrated intermediate portion 106 connects the labial portion 102 to the lingual portion 110 and has a narrower mesio-distal width than the labial portion 102 such that the intermediate portion 106 fits between the two wings of the second tie wing 46. In other constructions the intermediate portion 106 may have the same mesio-distal width as the labial portion 102 or may have a smaller mesio-distal width.

The illustrated lingual portion 110 engages the lingual resting groove 50 while in the open position and includes a lingual end 130 (see FIGS. 5 and 6) that has is shaped labially. The lingual portion 110 is sized to be received within the occlusal-gingival opening 54 and has a smaller mesio-distal width than the labial portion 102. The illustrated lingual portion 110 has the same mesio-distal width as the intermediate portion 106, although different mesio-distal widths are possible.

Turning now to FIG. 2, the bracket 14 is shown with the occlusal side surface 70 illustrated on the occlusal portion 94 of the body 26. In addition, a slot 134 is illustrated in the occlusal portion 94 that extends occlusally from the occlusal side surface 70 and lingually from a labial face 136. The slot 134 allows the tool to engage the cut-out 122 such that the tool may move the shutter 18 between the open position and the closed position.

Figure 5:
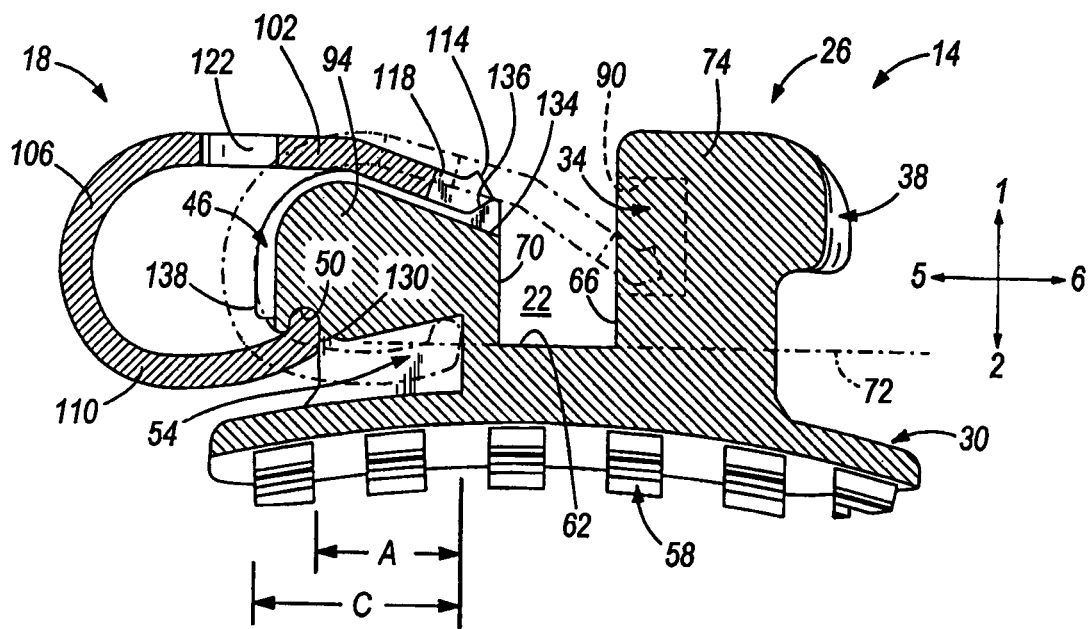
FIG. 5 is a section view of the self-ligating orthodontic bracket of taken along the section-line 5-5 in FIG. 4.
Figure 6:
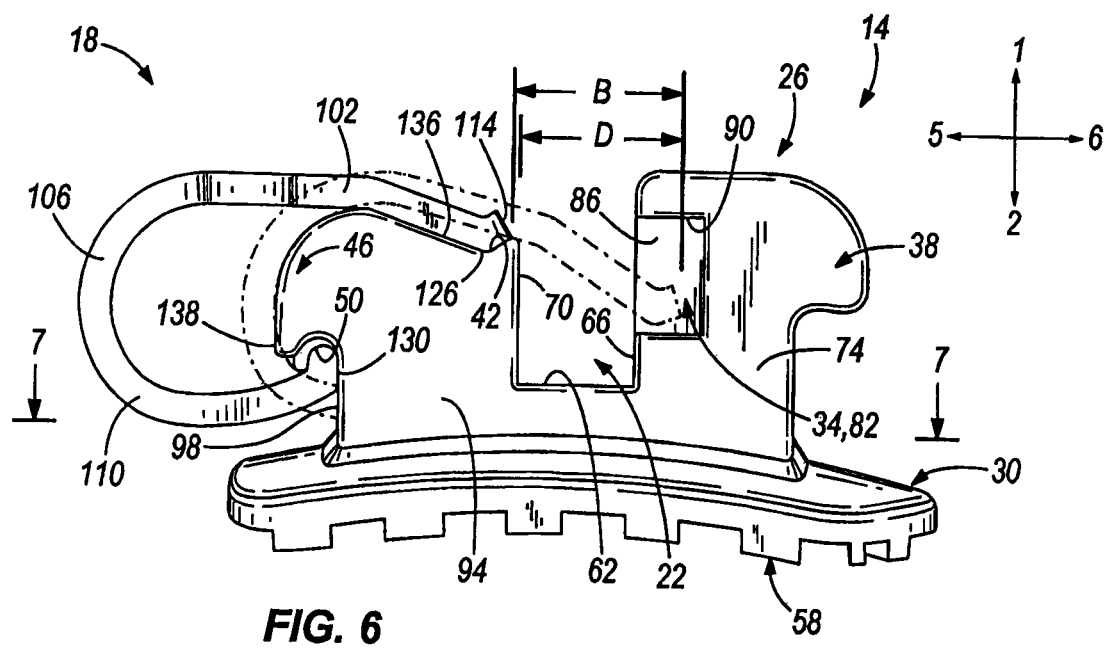
FIG. 6 is a side view of the self-ligating orthodontic bracket of FIG. 1.

FIGS. 5 and 6 illustrate the shutter 18 in the open position in solid lines and in the closed position in broken lines. The occlusal-gingival opening 54 is intersected by a mesio-gingival reference plane defined by the lingual surface 62 of the archwire slot 22. In the illustrated embodiment, the occlusal-gingival opening 54 does not extend entirely through the bracket 14, and thus no portion of the opening is positioned directly lingually of the archwire slot 22.

An illustrated distance A is defined by the occlusal-gingival distance between the lingual end 130 in the closed position and the lingual end 130 in the open position. An illustrated distance B is defined by the occlusal-gingival distance between the labial end 114 in the closed position and the labial end 114 in the open position. An illustrated distance C is defined by the occlusal-gingival distance from the lingual end 130 in the closed position to an occlusal edge 138 of the second tie wing 46. An illustrated distance D is defined by the occlusal-gingival distance between the labial end 114 in the closed position and the occlusal side surface 70.

In the illustrated construction, the distance A is about 1.0 millimeters, the distance B is about 1.2 millimeters, the distance C is about 1.4 millimeters, and the distance D is about 1.1 millimeters. In other constructions the distance A may be between about 0.5 and 2.0 millimeters, the distance B may be between about 0.6 and 2.4 millimeters, the distance C may be between about 0.7 and 2.8 millimeters, and the distance D may be between about 0.5 and 2.2 millimeters. In the open position the lingual end 130 is disposed in the lingual resting groove 50 at an open lingual location and the labial end 114 is disposed in the labial resting groove 42 at an open labial location. In the closed position the lingual end 130 is disposed in the occlusal-gingival opening 54 at a closed lingual location and the labial end 114 is disposed in the receiving area 34 at a closed labial location.

In operation, the bracket 14 is attached to the tooth with the attachment portion 58. The shutter 18 is moved to the open position with the labial end 114 disposed in the labial resting groove 42, the lingual end 130 disposed in the lingual resting groove 50, and the shutter 18 is substantially free of contact with the second tie wing 46. The appropriate archwire is fit into the archwire slot 22, and the tool engages the cut-out 122 and moves the shutter 18 out of the open position such that the labial end 114 leaves the labial resting groove 42 and the lingual end 130 leaves the lingual resting groove 50. The shutter 18 is moved over the archwire and into the closed position such that the labial end 114 is disposed within the receiving area 34 and the lingual end 130 is disposed within the occlusal-gingival opening 54. Once in the closed position, the shutter 18 inhibits the archwire from moving in the labial direction such that the archwire slot 22 and the shutter 18 cooperate to inhibit the movement of the archwire in the labial, lingual, occlusal, and gingival directions.

To remove the archwire, the tool is engaged with the cut-out 122 and the shutter 18 is moved from the closed position to the open position such that access is provided to the archwire slot 22 and the archwire may be removed.

Figure 7:
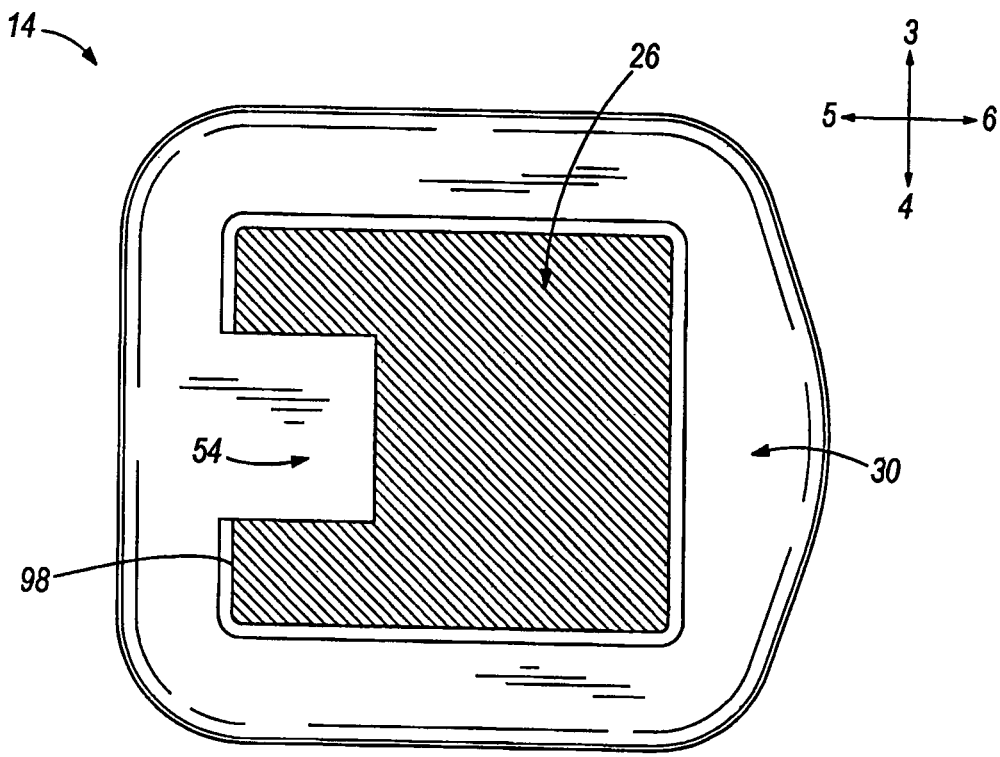
FIG. 7 is a section view of the self-ligating orthodontic bracket taken along the section-line 7-7 in FIG. 6.
Figure 8:
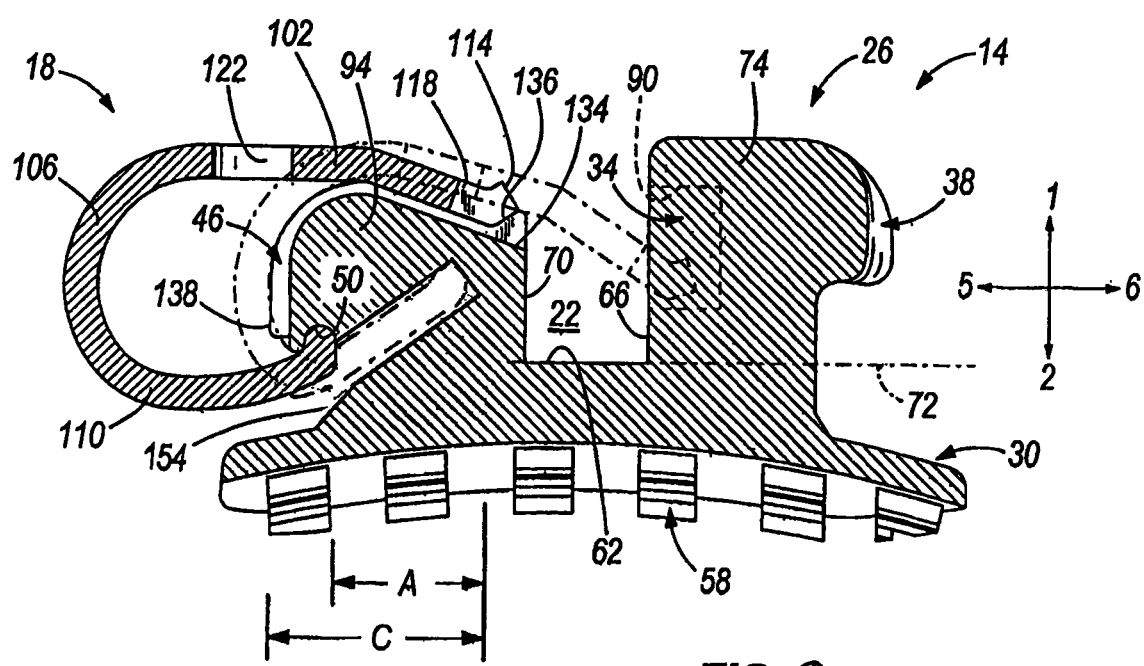
FIG. 8 is a section view, similar to the section view of FIG. 7, of a different self-ligating orthodontic bracket embodying aspects of the present invention.

FIG. 8 illustrates a slightly different bracket, which is shown in a section view similar to the section view of FIG. 7. In the embodiment of FIG. 8, all aspects of the bracket are substantially identical to the bracket of FIG. 7 with the exception of the position and orientation of an occlusal-gingival opening 154. In FIG. 8, the opening 154 is angled relative to the gingival-occlusal axis at an angle of about forty-five degrees. As with the previous embodiment, the clip 18 in FIG. 18 is highly resilient, and its resiliency will hold the clip in either of its open position (solid lines in FIG. 8) or closed position (broken lines in FIG. 8).

In addition to the constructions shown in FIGS. 1-8, the bracket 14 may be formed as a lingual bracket in which case the attachment portion 58 would attach the bracket 14 to the lingual side of the tooth and all references to labial and lingual would be reversed.

Thus, the invention provides, among other things, a self-ligating orthodontic bracket assembly. Various features and advantages of the invention are set forth in the following claims.

The invention claimed is:

1. A self-ligating orthodontic bracket comprising:
a base for attaching the bracket to a tooth;
a body having an archwire slot defined at least partially by a side surface and a lingual surface, wherein a mesio-gingival reference plane is tangent to a lingual-most point of the lingual surface, the body further having an occlusal-gingival opening in a first side of the body, wherein the reference plane intersects the opening, wherein the body further includes at least one tie wing on the first side of the body; and
a locking shutter coupled to the body and having a closed position where access to the archwire slot is inhibited and an open position where access to the archwire slot is permitted, wherein the locking shutter includes a lingual end located in the occlusal-gingival opening in said first side of said body and located at a closed lingual location relative to said first side of said body when the locking shutter is in the closed position, and wherein the lingual end is located at an open lingual location relative to said first side of said body when the locking shutter is in the open position, wherein the locking shutter further includes a labial end located at a closed labial location when the locking shutter is in the closed position and at an open labial location when the locking shutter is in the open position, wherein the side surface is closer to the open labial location than to the closed labial location, and wherein a first occlusal-gingival distance from the closed lingual location to the open lingual location is at least about 70% of a second occlusal-gingival distance from the closed labial location the side surface and wherein said lingual end of said shutter travels substantially along an essentially continuous planar surface of said occlusal-gingival opening and not away from said base as said lingual end moves from said closed lingual location to an open shutter position in which access to the archwire slot by said archwire is permitted.

2. The self-ligating bracket of claim 1, wherein the side surface defines an occlusal side of the archwire slot.

3. The self-ligating bracket of claim 1, wherein the first occlusal-gingival distance is at least about 80% of the second occlusal-gingival distance.

4. The self-ligating bracket of claim 1, wherein the first occlusal-gingival distance is at least about 90% of the second occlusal-gingival distance.

5. The self-ligating bracket of claim 1, wherein the body further includes a lingual resting groove in which the lingual end of the locking shutter is positioned when the locking shutter is in the open position.

6. The self-ligating bracket of claim 5, wherein the resting groove is positioned outside of the occlusal-gingival opening.

7. The self-ligating bracket of claim 1, wherein the opening is in a first side of the body, wherein the body further includes at least one tie wing on the first side of the body, and wherein the locking shutter is substantially free of contact with the tie wing when the locking shutter is in the open position.

8. The self-ligating bracket of claim 1, wherein the locking shutter includes a cut out adapted to receive an opening tool, and wherein the body includes a labial face and a slot in the labial face, the slot being aligned with the cut out when the locking shutter is in the closed position.

9. A self-ligating orthodontic bracket comprising:
a base for attaching the bracket to a tooth;
a body having an archwire slot defined at least partially by a lingual surface, wherein a mesio-gingival reference plane is tangent to a lingual-most point of the lingual surface, the body further having an occlusal-gingival opening in a first side of the body, wherein the reference plane intersects the opening, wherein the body further includes at least one tie wing on the first side of the body; and
a locking shutter coupled to the body having a closed position where access to the archwire slot is inhibited and an open position where access to the archwire slot is permitted, wherein the locking shutter includes a lingual end located in the occlusal-gingival opening in said first side of said body and located at a closed lingual location relative said first side of said body when the locking shutter is in the closed position, and the lingual end being located at an open lingual location relative said first side of said body when the locking shutter is in the open position, and wherein said lingual end of said shutter travels substantially only along an essentially continuous planar surface of said occlusal-gingival opening and not away from said base as said lingual end moves from said closed lingual location to an open shutter position in which access to the archwire slot by said archwire is permitted.

10. The self-ligating bracket of claim 9, wherein the first occlusal-gingival distance is at least about 65% of the second occlusal-gingival distance.

11. The self-ligating bracket of claim 9, wherein the first occlusal-gingival distance is at least about 70% of the second occlusal-gingival distance.

12. The self-ligating bracket of claim 9, wherein the body further includes a resting groove in which the lingual end of the locking shutter is positioned when the locking shutter is in the open position.

13. The self-ligating bracket of claim 12, wherein the resting groove is positioned outside of the occlusal-gingival opening.

14. The self-ligating bracket of claim 9, wherein the locking shutter is substantially free of contact with the tie wing when the locking shutter is in the open position.

15. The self-ligating bracket of claim 9, wherein the locking shutter includes a cut out adapted to receive an opening tool, and wherein the body includes a labial face and a slot in the labial face, the slot being aligned with the cut out when the locking shutter is in the closed position.

16. The self-ligating bracket of claim 9, wherein said essentially continuous planar surface is angled between about 10 degrees and about 80 degrees relative to the reference plane.

17. The self-ligating bracket of claim 9, wherein said essentially continuous planar surface is angled between about 30 degrees and about 60 degrees relative to the reference plane.

* * * * *